United States Patent [19]

Kaplan et al.

[11] Patent Number: 4,607,011

[45] Date of Patent: Aug. 19, 1986

[54] ACCUMULATION AND ISOLATION OF N-ACYLPHOSPHATIDYLSERINE

[75] Inventors: Samuel Kaplan; Timothy J. Donohue; Brian D. Cain, all of Champaign, Ill.

[73] Assignee: Board of Trustees, University of Illinois, Urbana, Ill.

[21] Appl. No.: 721,504

[22] Filed: Apr. 10, 1985

Related U.S. Application Data

[63] Continuation of Ser. No. 380,369, May 20, 1982, abandoned.

[51] Int. Cl.$^4$ .......................... C12P 9/00; C12P 1/00
[52] U.S. Cl. ..................................... 435/131; 435/41; 435/106; 435/128; 435/132; 435/134; 435/161; 435/822
[58] Field of Search .................. 435/41, 106, 161, 128, 435/131, 132, 134, 813, 822

[56] References Cited

PUBLICATIONS

Albert L. Lehninger; Biochemistry, Second Edition, 1975, pp. 287–290.
Timothy J. Donohue et al., Biochemistry, 1982, vol. 21, pp. 2765–2773.
Donald R. Lueking et al.; The Journal of Biological Chemistry, vol. 253, No. 2, 1978, pp. 451–457.
W. R. Sistrom, Journal of General Microbiology, vol. 22, 1960, pp. 778–785.
W. R. Sistrom, Journal of General Microbiology, (1962), vol. 28, pp. 607–616.
Robert T. Fraley et al., The Journal of Biological Chemistry, vol. 253, No. 2, 1977, pp. 458–464.

*Primary Examiner*—Sidney Marantz
*Assistant Examiner*—William J. Herald
*Attorney, Agent, or Firm*—Philip Hill

[57] ABSTRACT

A phospholipid mixture, rich in N-acylphosphatidylserine (NAPS), is produced by growth of certain bacterial cultures in media containing effective amounts of tris (hydroxymethyl) aminomethane. NAPS may be isolated in high purity by chromatographic techniques.

8 Claims, 2 Drawing Figures

ACCUMULATION AND ISOLATION OF N-ACYLPHOSPHATIDYLSERINE

This invention was made in the course of research work supported in part by grants from the National Institute of Health and the National Science Foundation.

This application is a continuation, of application Ser. No. 380,369, filed May 20, 1982, now abandoned.

BACKGROUND OF THE INVENTION

Phospholipids are a major component of biological membranes and the fluid mosaic model proposes that a phospholipid bilayer constitutes the basic unit of biological membrane structure. This phospholipid bilayer comprises a structural matrix of biological membranes with other membrane components either integral or peripheral to the bilayer. Phospholipids are an important component in such membrane functions as the constitution of a barrier to permeability and the activation of membrane-bound enzymes. The physical properties of phospholipids in the bilayer, their spatial arrangement, and their interactions with membrane proteins have been studied extensively. Their structural and functional importance in biological membranes has also generated considerable interest in the regulation and metabolism of various phospholipid species. Consequently many investigations of the control of membrane assembly have focused on the control of phospholipid synthesis and the relationship between phospholipid synthesis and membrane structure and function.

The biosynthetic pathway for phospholipids of *Escherichia coli* has been elucidated by developing *in vitro* enzyme assays for these activities. These investigations have established that phosphatidylethanolamine (PE) is synthesized from CDP-diglyceride through the sequential activities of phosphatidylserine synthetase and phosphatidylserine decarboxylase. Phosphatidylglycerol (PG) is the product of a separate pathway which diverged at the level of CDP-diglyceride. The study of phospholipid metabolism has been further facilitated by selection of temperature-sensitive mutant strains defective in phospholipid synthesis, with any alterations manifested in the accumulation of known pathway products and intermediates. For example, in a phosphatidylserine synthetase deficient mutant, cardiolipin increased and the amount of PE was reduced, while phosphatidylserine (PS) accumulated in a phosphatidylserine decarboxylase defective strain. However, it has been recently reported that a strain virtually devoid of PG has elevated levels of glycolipids, indicating an adjustment in cellular metabolism in response to the membrane phospholipid imbalance. The application of recombinant DNA techniques has allowed the construction of *E. coli* strains which overproduce phospholipid biosynthetic enzymes, but these strains do not possess altered cellular phospholipid compositions.

Physiological investigations of phospholipid enzymology have shown that it is restricted to the inner membrane of gram negative bacteria. Unfortunately, little has been reported on the localization of the phospholipid biosynthetic enzymes in the photosynthetic bacteria which possess an extensive intracytoplasmic membrane system (ICM).

The facultative photoheterotrophic bacterium *Rhodopseudomonas sphaeroides* has provided an attractive system in which to study membrane biogenesis and differentiation. When growing chemoheterotrophically, *R. sphaeroides* contains a typical gram-negative outer membrane and a cytoplasmic membrane. However, photoheterotrophic growth conditions induce the differentiation of the cytoplasmic membrane, resulting in the synthesis of an intracytoplasmic membrane system which houses the photosynthetic apparatus of the cell. Studies on the regulation of intracytoplasmic membrane assembly, employing synchronously dividing populations of *R. sphaeroides*, have shown that, while insertion of protein and photopigments into the intracytoplasmic membrane occurs continuously throughout the cell cycle, accumulation of phospholipids within the intracytoplasmic membrane occurs discontinuously with respect to the cell cycle. This discontinuity in phospholipid incorporation results from the bulk transfer of phospholipids from outside the intracytoplasmic membrane into the intracytoplasmic membrane concurrent with cell division.

Extensive studies on the growth of *R. sphaeroides* have led to the identification of a new phospholipid, normally present in minor proportions. The major phospholipid species generally found are PG, PE, and phosphatidylcholine (PC). It has now been found that varying the composition of the culture medium can surprisingly affect the production of particular phospholipids such as N-acylphosphatidylserine (NAPS).

SUMMARY OF THE INVENTION

This invention relates to a process for the production of phospholipids, particularly N-acylphosphatidylserine (NAPS), by growth of selected bacterial strains in a growth medium containing tris (hydroxymethyl) aminomethane (Tris). The process of this invention includes the steps of:
 (a) providing a bacterial culture comprising cells selected from the class consisting of *Rhodopseudomonas sphaeroides, Rhodopseudomonas capsulata*, and *Paracoccus denitrificans*;
 (b) growing the cells in a neutral phosphate medium, additionally comprising tris (hydroxymethyl) aminomethane;
 (c) isolating the cell culture from the medium; and
 (d) recovering phospholipids from the isolated cell culture.

This invention additionally relates to additional processing for the isolation of NAPS from phospholipid mixtures by the use of selected chromatographic techniques.

This invention additionally relates to a novel phospholipid product. The acyl substituents of the NAPS product of this invention are derived from fatty acids having 16 or 18 carbon atoms per molecule, with a major proportion having one carbon-carbon double bond per molecule.

DESCRIPTION OF THE DRAWINGS

The accompanying drawings are illustrative of aspects of this invention.

DETAILED DESCRIPTION OF THE INVENTION

Figure 1:
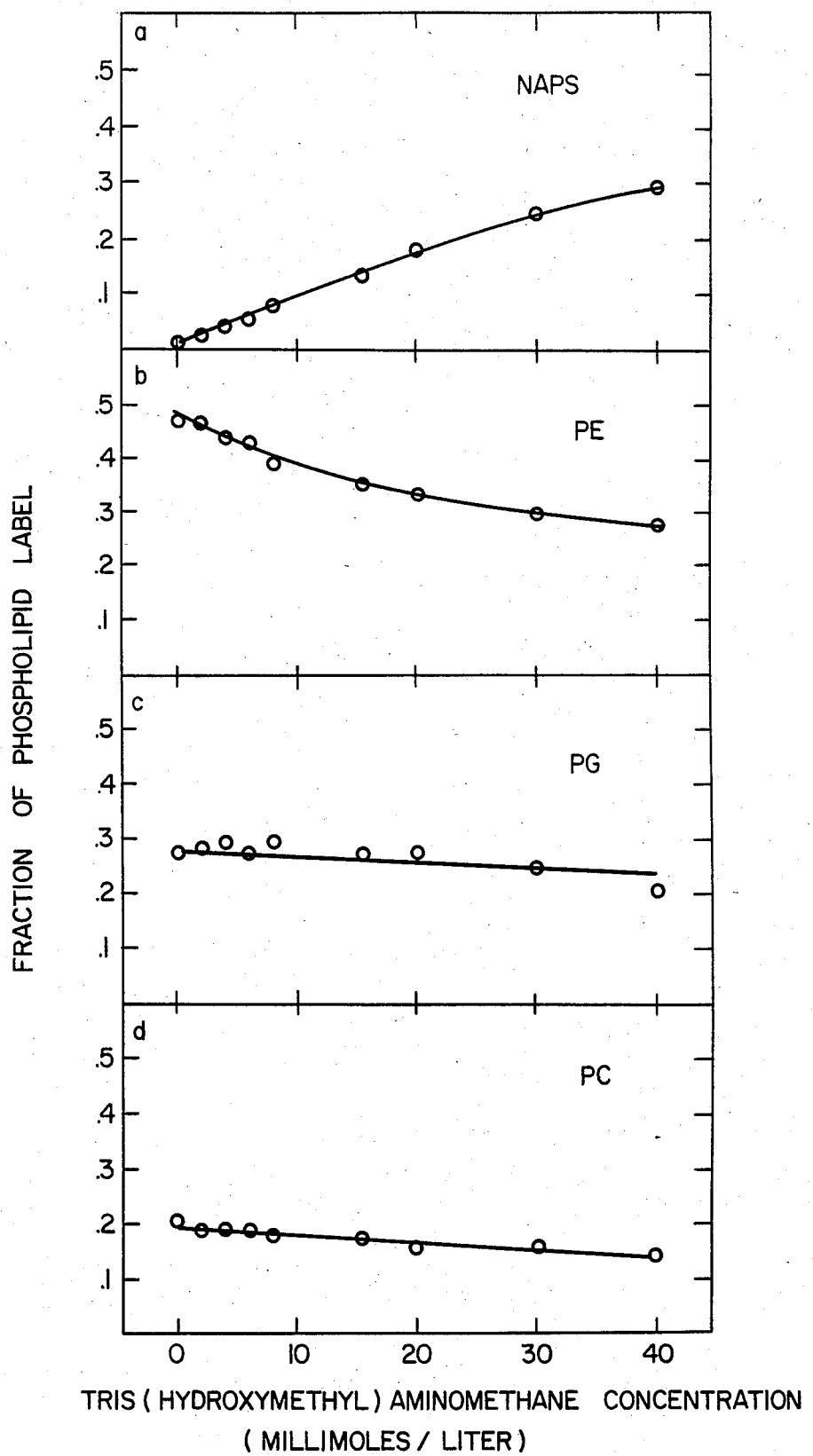
FIG. 1 presents, in graphical form, the variation in relative occurrence of the major phospholipids in response to variations in the concentration of Tris, ranging up to 40 millimoles/liter.

This invention relates to novel growth conditions for the accumulation of NAPS and subsequent isolation of the novel phospholipid product in substantially pure condition. Essential steps for the production of NAPS include:

(a) providing a bacterial culture comprising cells selected from the class consisting of *Rhodopseudomonas sphaeroides, Rhodopseudomonas capsulata,* and *Paracoccus denitrificans;*

(b) growing the cells in a neutral phosphate medium, additionally comprising tris (hydroxymethyl) aminomethane;

(c) isolating the cell culture from the medium; and (d) recovering phospholipids from the isolated cell culture.

Additional processing for isolation of NAPS from typical phospholipids associated therewith includes at least the steps of:

(a) providing an extract of the phospholipid mixture in a chloroform solvent;

(b) passing the chloroform extract of phospholipids over a first absorbent phase, comprising silica gel;

(c) eluting the phospholipids from the silica gel with a carbinol solvent;

(d) transferring the eluted phospholipids from the carbinol solvent to a chloroform solvent;

(e) passing the chloroform solution from step (d) over a second absorbent phase, comprising diethyl aminoethyl cellulose;

(f) eluting the diethyl aminoethyl cellulose phase with a mixed solvent comprising methanol and chloroform;

(g) subsequently eluting the diethyl aminoethyl cellulose phase with an acidic solvent comprising chloroform and acetic acid; and (h) isolating N-acylphosphatidylserine from the acidic solvent.

A new phospholipid has been identified in strains of *Rhodopseudomonas sphaeroides, Rhodopseudomonas capsulata,* and *Paracoccus denitrificans.* However, the normal level of this phospholipid is extremely low, less than 0.5% of the total cellular phospholipid. The process of this invention provides a procedure for causing these cells to accumulate large quantities (up to 40% of total cellular phospholipid) of this phospholipid by the addition of [Tris (Hydroxylmethyl) aminomethane] to the cell culture medium. The final level of NAPS is closely dependent upon Tris addition and the accumulation of NAPS occurs with from about 3 to about 5 minutes after Tris addition. The structure of NAPS has been rigorously established in the course of studying the synthesis and regulation of photosynthetic membranes in *Rhodopseudomonas sphaeroides.*

Other N-acylphospholipids are known; N-acylphosphatidylethanolamine occurs, for example, in low levels in plant seeds. However, unlike N-acylderivatives of phosphatidylethanolamine, NAPS is an acidic phospholipid which is of value in membrane fusion experiments.

A previously described natural occurence of NAPS is highly problematical. No procedure or process has been described which will influence its abundance. Synthetic NAPS can be prepared in very low yield starting from a fatty acid anhydride and purified brain phosphatidylserine, using N,N-dimethyl-4-aminopyridine as a catalyst. The simple addition of Tris to the growth medium of certain bacterial strains mentioned above results in a surprising accumulation of NAPS. No effect on growth of the culture is observed. Depending upon Tris concentration, the final level of accumulated NAPS will vary. This can be accomplished with cells of *R.sphaeroides* or *R. capsulata* grown chemoheterotrophically or photoheterotrophically, or with cells of *P. denitrificans* grown chemoheterotrophically. Cells can be grown on defined media at any growth temperature at which the bacteria can grow. Certain media supplements, such as yeast extract or casamino acids are antagonistic to the Tris-induced accumulation of NAPS and, consequently, complex media containing such supplements may not afford attractive yields of NAPS. Under any growth conditions in the absence of Tris, only low levels (0.5%) of NAPS are formed. Growth of the cells and the procedure for NAPS accumulation and eventual isolation and purification are quite inexpensive.

Purification of the novel phospholipid has been accomplished by column chromatography on silicic acid and diethylaminoethyl cellulose followed by preparative thin layer chromatography. A combination of spectroscopic and chemical techniques were used to identify the unknown phospholipid as NAPS. Infrared spectroscopy revealed the presence of both ester and amide bonds and the proton nuclear magnetic resonance spectrum indicated the presence of three acyl chains per phospholipid. Chemical studies confirmed the presence of a glycerylphosphorylserine moiety in the molecule and yielded three fatty acyl chains per hydrolyzed phospholipid. The fatty acid composition of the phospholipid was approximately 85% vaccenic acid, 9% stearic acid, 5% palmitic acid and 1% palmitoleic acid, which is essentially identical to the fatty acid composition of whole cell phospholipid preparations from *R. sphaeroides.* Chemical synthesis of an N-acylphosphatidylserine from beef brain phosphatidylserine and palmitic anhydride gave a product with characteristics similar to the naturally occurring material isolated from *R. sphaeroides.*

NAPS provides a useful research tool for studies of membrane structure and function. NAPS also shows great promise relative to liposome formation and membrane fusion technologies for delivering substances into a variety of cell types. Its negative charge and the presence of three fatty acyl chains per molecule is unique. It has approximately 50% more caloric value per mole of phospholipid and should find use as a lipid supplement.

Some bacterial strains exhibit the growth of NAPS, as generally described herein, in media containing Tris. This novel production and accumulation has been observed with certain members of the genus Rhodospirillaceae. These include *R. sphaeroides,* strains M29-5, NCIB 8253, WS 8, L, and 2.4.7 (but not wild strains 2.4.1 and R52); *R. capsulata,* strain B-10; and *P. denitrificans,* strain ATCC 13543.

Any defined growth medium may be employed, preferably a minimal medium, with the addition of Tris in amounts up to a concentration of about 100 millimoles per liter, preferably from about 15 to about 40 millimoles per liter. The medium may be supplemented with minor amounts (about 50 micrograms per milliliter) of methionine and leucine, as for example, with *R. sphaeroides,* strain M29-5. The pH value should be maintained at about 7.0. The phosphate concentration, like the Tris concentration, may be varied over a substantial range, but unlike the Tris concentration, does not affect the production and accumulation of NAPS.

Culture growth for *R. sphaeroides* or *R. capsulata* may be either photoheterotrophic or chemoheterotrophic, at any conventional growth temperature for the particular cells, preferably about 32° C. In a preferred photoheterotrophic procedure, the culture is grown with a sparging gas mixture, containing approximately 95 vol. % nitrogen and 5 vol. % carbon dioxide, and with continuous saturating illumination (600 foot candles) provided, for example, by a bank of Lumline lamps. In a preferred chemoheterotrophic procedure, the culture is grown with a second sparging gas mixture, containing approximately 74 vol. % nitrogen, 25 vol. % oxygen, and 1 vol. % carbon dioxide. Cells are adapted to growth in the selected medium for at least six culture doublings prior to use. During culture growth through some six culture doublings a final cell density of about $1 \times 10^9$ cells per milliliter is achieved.

Recovery of phospholipids rich in NAPS from the bacterial cells is generally accomplished by extraction with a halogenated hydrocarbon solvent, such as chloroform. Extraneous material is separated by first distributing the phospholipids upon a silica gel, or silicic acid, absorbent phase in a chromatographic column and washing further with chloroform. The concentrated phospholipids are then recovered by elution of the absorbent phase with a polar carbinol solvent, preferably methanol. After recovering the phospholipids from the alcohol phase, as by evaporation of the polar solvent, they are once again dissolved in the halohydrocarbon, such as chloroform, and distributed upon a second absorbent phase, generally comprising diethyl aminoethyl cellulose. Elution with a chloroform:methanol mixture removed substantial quantities of phospholipids such as PC. Increasing the methanol content of the mixture removed principally the phospholipid, PE. Thereafter, elution with a chloroform-acetic acid mixture removed substantially all of the NAPS in about 90% purity. Other phospholipids, principally PG, remained on the second absorbent phase and were removed by elution with a chloroform-acetic acid-ammonium acetate mixture. Further purification of NAPS was effected by additional applications of thin-layer chromatography.

The following preparations and procedures are exemplary, without limitation, of the processes of this invention.

EXAMPLE I

*Rhodopseudomonas sphaeroides* M29-5, a leucine and methionine auxotroph of the wild-type strain 2.4.7, was grown photoheterotrophically in completely filled culture vessels using a low phosphate (2 mM phosphate, 20 mM Tris, pH 7.0) modification of the succinic acid minimal medium. Control experiments showed that the growth of *R. sphaeroides* M29-5 was not measurably affected by the low phosphate to yield fractions rich in, respectively, PC, PE, NAPS, and PG. The respective fractions were taken to dryness by rotary evaporation and the phospholipids were purified using preparative thin layer plates.

Individual phospholipid species were resolved using a two-dimensional thin layer chromatography system. Silica gel G plates impregnated with 0.4M boric acid, used for analytical purposes, were 0.25 mm. thick while preparative thin layer plates were 0.5 mm. Chloroform:methanol:water:ammonium hydroxide (70:30:3:2) constituted the first-dimension solvent system while chloroform:methanol: water (65:35:5) was used for development in the second-dimension. Plates were dried under a nitrogen atmosphere between the first and second dimensions. Detection of phospholipids was accomplished by iodine staining or, in some cases when labeled samples were used, by autoradiography. The amount of radioactivity in each of the phospholipid species was determined by scraping the phospholipid-containing gel from the thin layer plates directly into scintillation vials using a toluene based scintillation fluid. Non-radioactively labeled phospholipids were quantified by lipid phosphorous assays. Residual silica gel in the purified phospholipid samples was removed by chromatography on the silicic acid column as described in Example II.

EXAMPLE IV

Elemental analysis of pure NAPS revealed that, by weight, NAPS was composed of 581.0% carbon, 9.3% hydrogen, 3.5% phosphorous and 1.4% nitrogen. Pure *R. sphaeroides* PG was found to contain 4.2% phosphorous by weight so that if medium (generation time of 150 to 180 minutes at 32° C.). Growth of the cells was allowed to continue for approximately 6 culture doublings (final cell density approximately $1 \times 10^9$ cells per ml) before sampling.

Phospholipids were extracted into chloroform and the resulting chloroform fractions were washed once with an equal volume of 1% (w/v) NaCl.

EXAMPLE II

Extraction of whole cell phospholipids was accomplished as in Example I. The extracted phospholipids were separated from photopigments by repeated precipitation of the phospholipids in ice-cold acetone followed by chromatography on a column (4×20 cm) of silicic acid H. The phospholipid-containing methanol eluate of the silicic acid column was taken to dryness under reduced pressure by rotary evaporation, suspended in a minimal volume of chloroform and stored in Teflon-lined, screwcapped tubes at −20° C.

EXAMPLE III

Purification of an individual phospholipid species from *R. sphaeroides* was accomplished using the following general protocol. Bulk phospholipids in chloroform (either with or without the acetone precipitation step) were applied to a column (2×20 cm) of Cellex D which had been previously equiliberated with chloroform. Fractions enriched in individual phospholipids were eluted from the column employing successive solvent washes comprising (a) chloroform:methanol (9:1); (b) chloroform:methanol (7:3); (c) chloroform:acetic acid (3:1); and (d) chloroform:acetic acid (3:1) containing 10 millimoles/liter of ammonium acetate, the assumption is made that NAPS contains one phosphorous per molecule then the finding that nitrogen accounted for 1.4% of the weight of NAPS revealed that NAPS contains approximately one nitrogen atom per phospholipid molecule. A minimum molecular weight for NAPS of approximately 1000 was obtained using the elemental analysis data and the assumption that there was one nitrogen atom per phospholipid molecule.

EXAMPLE V

Infrared spectra were obtained from KBr pellets containing a mixture of approximately one to two mg of phospholipid per 100 mg of KBr using a Beckman IRI2 double-beam infrared spectrophotometer. All spectra were recorded at room temperature against a reference KBr pellet. The ability to derive complete and definitive structural information from IR spectra of phospholipids is limited by the existence of many IR-absorbing functional groups in the molecule. Although the IR spectrum of NAPS was similar to those of other glycerophosphatides, strong absorption bands at approximately 1575, 3200 and 3300 cm$^{-1}$ were indicative of the presence of an amide bond in the molecule. Absorption at these wavenumbers was not found in the spectra of other pure glycerophosphatides, but strong signals in these regions are characteristic of the amide bond of sphingolipids. In contrast, strong absorption at 1750 cm$^{-1}$ (a region of absorption assigned to the stretching of the ester carbonyl groups of glycerophosphatides) is not seen in sphingolipids. Therefore, absorption by NAPS at 1750 cm$^{-1}$, as well as at 1575, 3200 and 3300 cm$^{-1}$, indicated the presence of both the ester carbonyl groups found in all glycerophosphatides and amide bond.

EXAMPLE VI

Independent confirmation of the occurence of serine and glycerol in NAPS was also obtained after hydrolysis of NAPS in constant boiling (6N) HCl at 110° C. for 3 or 6 hours. Glycerol phosphate and serine were identified as water-soluble products of acid hydrolysis using paper chromatography. The presence of serine in the hydrolysates was also confirmed by analysis of a portion of the sample on an amino acid analyzer.

EXAMPLE VII

Analysis of the acyl ester content of NAPS as well as bulk phospholipid from R. sphaeroides M29-5 indicated approximately 2 acyl ester equivalents per equivalent of phosphorous (Table 1). Acid (2N HCl) or base (0.5N NaOH) catalyzed transmethylation increased the acyl ester to phosphorous ratio of NAPS to approximately 3 while the ratio for bulk phospholipid remained at two. Table 1 also shows that there were no detectable differences between the fatty acid composition of NAPS and bulk phospholipid from R. sphaeroides M29-5. Thus (i) the recovery of 3 fatty acyl methyl esters after treatment of NAPS with methanolic hydrochloric acid, (ii) the detection of one nitrogen per NAPS molecule together with the lack of reactivity of NAPS with aminogroup specific reagents, (iii) the indication of an amide bond in the IR spectrum of NAPS, and (iv) the identification of a glycerylphosphorylserine moiety were all consistent with the unknown phospholipid being an N-acylphosphatidylserine. However, the finding that mild alkaline methanolysis of the phospholipid also resulted in the formation of approximately 3 equivalents of fatty acyl methyl ester per molecule was unexpected.

TABLE I

| Fatty Acid Content and Composition | | |
|---|---|---|
| Sample | NAPS | Bulk Phospholipid |
| Acyl Ester/Phosphorous Ratio | | |
| Untreated | 1.7 ± 0.3 | 2.2 ± 0.3 |
| Transmethylated | 2.8 ± 0.2 | 2.0 ± 0.3 |
| Acyl Equivalents/Mole | 3.1 ± 0.3 | 2.1 ± 0.2 |
| Fatty Acid Composition | | |
| $C_{16:0}$ | 5.6 ± 0.4 | 6.1 ± 0.6 |
| $C_{16:1}$ | 1.0 ± 0.2 | 0.8 ± 0.1 |
| $C_{18:0}$ | 9.5 ± 0.8 | 11.3 ± 0.2 |
| $C_{18:1}$ | 84.2 ± 1.6 | 81.9 ± 1.3 |

The effect of Tris on the phospholipid composition of R. sphaeroides M29-5 is shown in FIG. 1. Cells were grown photoheterotrophically and steady-state labeled with [$^{32}$P]-orthophosphoric acid in succinic acid minimal medium supplemented with the indicated concentrations of Tris. At late exponential phase of growth, 0.6 ml samples were removed, the phospholipids extracted and the fraction of the total phospholipid label in each of the phospholipid species determined after resolution of the phospholipids as described in earlier Examples. The generation time of the cells was between 2.5 and 3.0 hours in all cases. The data are expressed as the fraction of the total phospholipid label in the individual phospholipid species. Total radioactivity applied per plate was approximately $3 \times 10^4$ cpm. Legend: a - NAPS, b - PE, c - PG, d - PC. The fraction of NAPS in the total phospholipids can be seen to increase linearly with the increase in Tris concentration in the medium.

Figure 2:
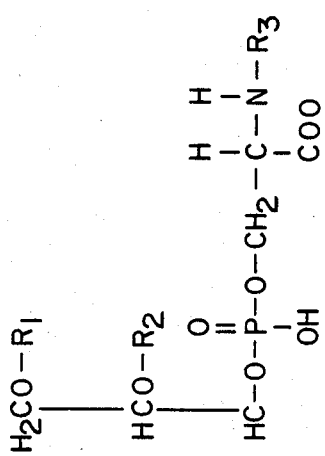
FIG. 2 is illustrative of the molecular structure of NAPS and additionally of the acyl substituents contained within the NAPS molecule.

The structure of NAPS, as deduced from the investigations set forth in the preceeding Examples, is presented in FIG. 2. The third acyl component ($R_3$) is shown linked to the amino function of the serine group. It is presumed that the various fatty acid chains, as set forth in Table I, are distributed randomly among the various acyl amide and ester linkages. The various fatty acid chains are set forth in structural detail, including the locus of the carbon-carbon unsaturation along the backbone chain.

We claim:

1. A process for the production of N-acylphosphatidylserine during the growth of selected bacterial cells, comprising the steps of:
   (a) providing a culture comprising bacterial cells selected from the class consisting of Rhodopseudomonas sphaeroides, Rhodopseudomonas capsulata, and Paracoccus denitrificans;
   (b) growing the bacterial cells in a neutral growth medium, said medium additionally comprising up to about 100 millimoles per liter of tris (hydroxymethyl) aminomethane;
   (c) isolating the growth of bacterial cells from the neutral medium;
   (d) separating a cellular phospholipid fraction from the isolated bacterial cells, said cellular phospholipid fraction comprising N-acylphosphatidylserine, by extraction therefrom with a polar organic solvent; and
   (e) recovering N-acylphosphatidylserine from the cellular phospholipid fraction.

2. The process of claim 1 wherein the cells are grown chemoheterotrophically.

3. The process of claim 1 wherein the cells of R. sphaeroides or R. capsulata are grown photoheterotrophically.

4. The process of claim 1 wherein the neutral growth medium is a minimal medium.

5. The process of claim 1 wherein the neutral growth medium is supplemented with minor amounts of methionine and leucine.

6. The process of claim 1 wherein the medium comprises from about 15 to about 40 millimoles per liter of tris (hydroxymethyl) aminomethane.

7. The process of claim 1 wherein the polar organic solvent is chloroform.

8. The process of claim 1 wherein the N-acylphosphatidylserine is recovered by chromatographic separation from the cellular phospholipid fraction.

* * * * *